United States Patent [19]

Koiso et al.

[11] Patent Number: 5,425,975
[45] Date of Patent: Jun. 20, 1995

[54] SHEET-SHAPED HEAT-GENERATING BODY

[75] Inventors: Yasuhiko Koiso, Hiratuka; Shigeo Ariki, Yokohama, both of Japan

[73] Assignee: Japan Pionics Co., Ltd., Tokyo, Japan

[21] Appl. No.: 299,802

[22] Filed: Sep. 1, 1994

Related U.S. Application Data

[63] Continuation of Ser. No. 976,668, Nov. 16, 1992, abandoned, which is a continuation of Ser. No. 607,674, Nov. 1, 1990, abandoned.

[30] Foreign Application Priority Data

Nov. 8, 1989 [JP] Japan ................................. 1-288781

[51] Int. Cl.6 .................. B32B 1/04; B32B 5/16; A61F 7/08
[52] U.S. Cl. ................... 428/74; 126/204; 126/206; 428/137; 428/138; 428/219; 428/220; 428/283; 428/289; 428/913; 607/96
[58] Field of Search ............ 126/204, 206, 263, 269, 126/271.1; 428/549, 74, 289, 246, 137, 138, 219, 220, 283, 913; 423/219; 128/403, 399

[56] References Cited

U.S. PATENT DOCUMENTS

| | | | |
|---|---|---|---|
| Re. 32,026 | 11/1985 | Yamashita et al. | 126/263 |
| 4,205,685 | 6/1980 | Yoshida et al. | 128/399 |
| 4,230,595 | 10/1980 | Yamaji et al. | 423/219 |
| 4,255,157 | 3/1981 | Yamaguchi et al. | 126/263 |
| 4,516,564 | 5/1985 | Koiso et al. | |
| 4,756,299 | 7/1988 | Podella | 126/263 |
| 4,955,360 | 9/1990 | Ogawa et al. | 126/263 |

FOREIGN PATENT DOCUMENTS 63-37181 2/1988 Japan .
64-42018 3/1989 Japan .

OTHER PUBLICATIONS

Patent Office of Japan, File Supplier JAPS, Tokyo, JP; & JP-A-1 201 253 (Japan Pionics *Abstract*.
Patent Office of Japan, File Supplier JAPS, Tokyo, JP; & JP-A-55 139 480 (Souei) *Abstract*.

*Primary Examiner*—James D. Withers
*Attorney, Agent, or Firm*—Oliff & Berridge

[57] ABSTRACT

A sheet-shaped heat-generating body comprising a sheet-shaped substrate comprising irregularly arranged fibers and having a multiplicity of gaps among the fibers, an oxidizable metal powder dispersed in and supported by the substrate, and an inorganic electrolyte solution containing activated carbon mixed and suspended therein with which the substrate supporting the oxidizable metal powder dispersed therein is impregnated. Since the entire structure of the sheet-shaped heat-generating body is integrated, with the fibrous and porous sheet-shaped substrate assuring uniform distribution and firm support of the oxidizable metal powder or the heat-generating substance, the body is flexible, is free from one-sided distribution of the heat-generating substance, and has excellent heat generating capability.

15 Claims, 2 Drawing Sheets

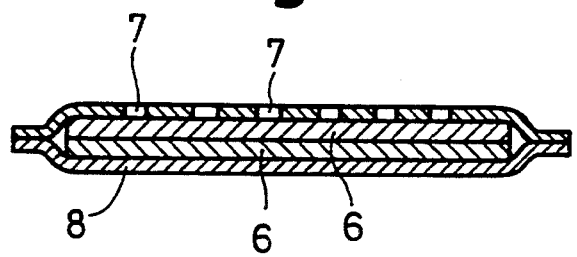
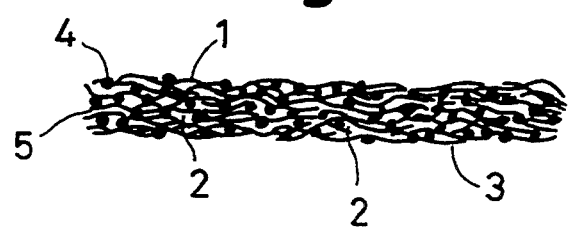
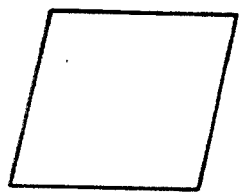  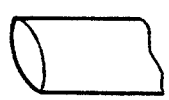 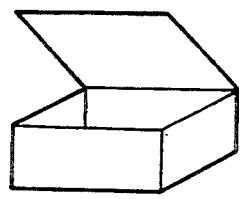

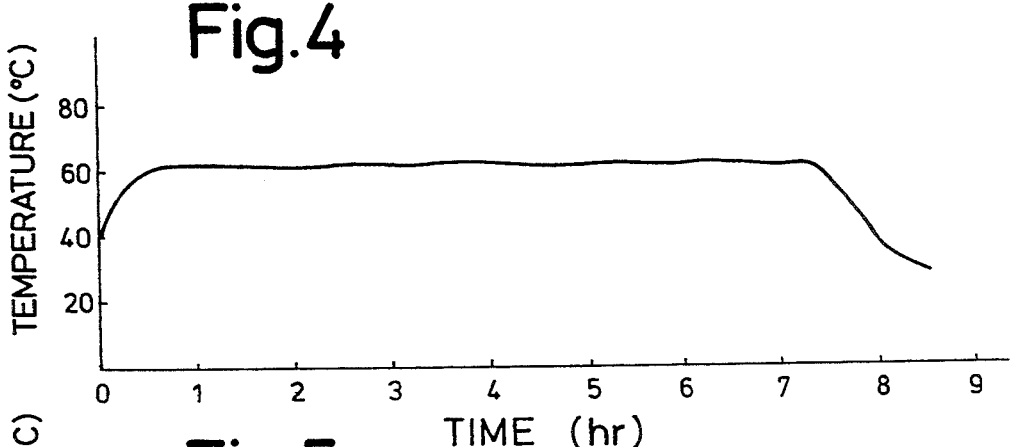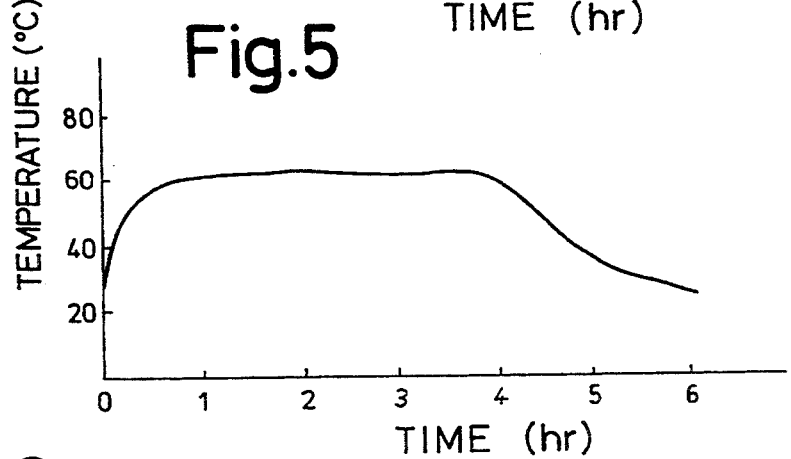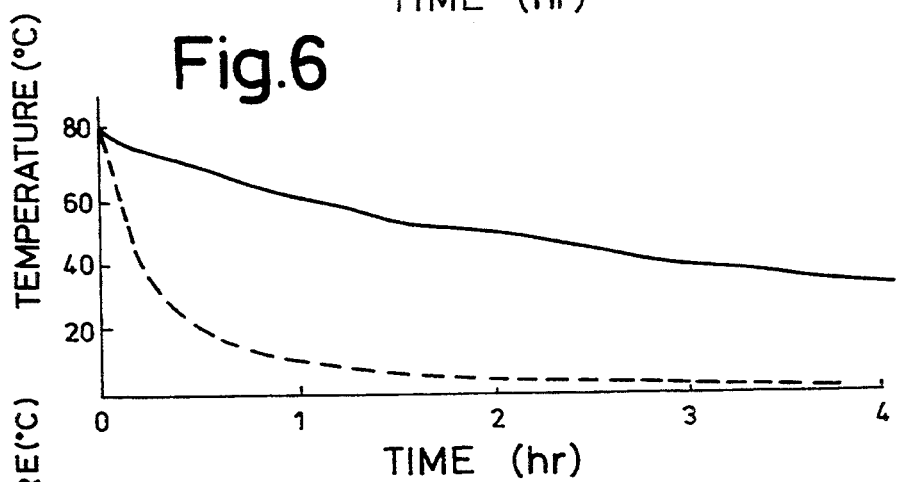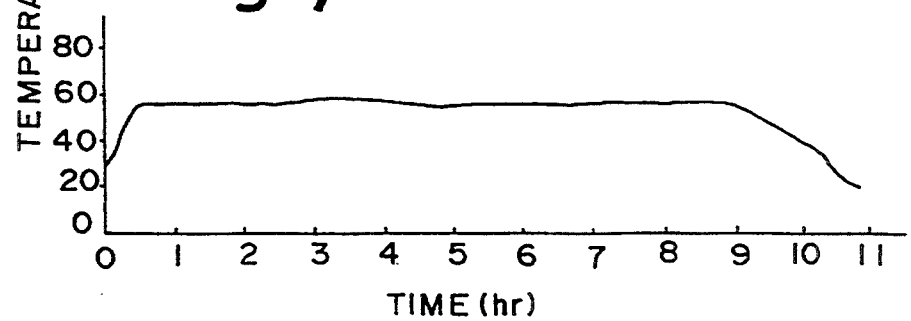

SHEET-SHAPED HEAT-GENERATING BODY

This is a continuation of application Ser. No. 07/967,668 filed Nov. 16, 1992, now abandoned, which is in turn a continuation of application Ser. No. 07/607,674 filed Nov. 1, 1990, now abandoned.

BACKGROUND OF THE INVENTION

1. Field of the Invention

The present invention relates to a sheet-shaped heat-generating body, and more specifically, to a sheet-shaped heat-generating body that is flexible and free from displacement or one-sided distribution of the heat-generating substance.

2. Description of the Related Art

Recently, a heat-generating body has been widely used as a type of warming means, for instance, as a disposable and portable body warmer. Such a heat-generating body comprises a heat-generating substance mainly consisting of an oxidizable metal powder such as iron powder or aluminum powder which is received in an air-permeable bag, and which is capable of generating heat upon contact with the air.

Although such a heat-generating body is advantageous in that it can be easily used, it entails the following defects. When the heat-generating body is used, for instance, to warm a human body or food, the heat-generating substance tends to displace downward under gravitation not only during movement of the human body or during transportation of the food but even while the heat-generating body is motionless. This leads to deformation of the heat-generating body, which can be uncomfortable or inconvenient to the user. In addition, the heat-generating characteristic of the heat-generating body per se may change, deteriorating its heat-generating performance.

In order to eliminate these defects, various proposals have been made on structures where a heat-generating substance is supported by a sheet-shaped substrate so as to prevent displacement of the heat-generating substance.

Such proposals include a method of supporting a heat-generating substance by a net-shaped member of metal gauze, plastic or gauze (Japanese Patent Laid-Open No. 84246/1978), a method of superimposing an oxidizable metal in the form of foil or the like on a sheet-shaped oxidation assistant comprising fiber of activated carbon, etc. impregnated with a chloride and water (Japanese Patent Laid-Open No. 37181/1988), and a method of supporting a compressed heat generating agent on paper (Japanese Utility Model Laid-Open No. 42018/1989).

However, since a heat-generating substance tends to mass when mixed with water, etc., it is very difficult, from the viewpoint of fabrication, to directly support a heat-generating substance on a net-shaped member while assuring uniform distribution. With a structure where an oxidizable metal in the form of, e.g., foil is superimposed on a sheet-shaped oxidation assistant, since the oxidizable metal and the oxidation assistant are not uniformly integrated together, sufficient heat generating performance cannot be expected. Further, a structure where a heat-generating agent is merely compressed onto and supported by paper, involves a risk that the heat-generating substance may separate from the paper during use.

SUMMARY OF THE INVENTION

The present inventors have conducted various studies to obtain a sheet-shaped heat-generating body of which the entire structure is integrated and free from the risk of separation of the heat-generating substance, which has excellent heat-generating capability, and which is flexible. As a result, they have found that, if a sheet-shaped substrate comprising irregularly arranged fibers and having a multiplicity of fine gaps is used, metal powder can be uniformly distributed and firmly supported without the risk of separation. The present inventors have thus accomplished the present invention. Therefore, an object of the present invention is to provide such a sheet-shaped heat-generating body.

A sheet-shaped heat-generating body according to the present invention comprises: a sheet-shaped substrate comprising irregularly arranged fibers and having a multiplicity of gaps among the fibers; an oxidizable metal powder dispersed in and supported by the substrate; and an inorganic electrolyte solution containing activated carbon mixed and suspended therein, the substrate supporting the oxidizable metal powder dispersed therein being impregnated with the inorganic electrolyte solution.

According to the present invention, a sheet-shaped substrate comprising irregularly arranged fibers and having a multiplicity of gaps is used, and an oxidizable metal powder is supported by the substrate.

The category of the material used to form the substrate is not specifically limited, but may be either organic fiber or inorganic fiber. Normally, however, organic fiber is used. Examples of organic fibers which may be used include sheets or non-woven fabrics of: natural fibers such as pulp, viscose rayon, cotton, hemp and wool; and synthetic fibers of polyethylene, polypropylene and nylon, and acrylic fibers. Among these, thick non-woven fabric of a natural fiber having a large gap ratio and a large water retention ratio is preferable, and a sheet-shaped non-woven fabric in which fibers made of wood pulp are irregularly arranged by a wet method or a dry method is suitable. For example, among the non-woven fabrics by the dry method, Quinocloth (KINO CLOTH, product of Honshu Seishi Kabushiki Kaisha) and BOLT (product of American Can Corp.) are preferable, and among the non-woven fabrics by the wet method, wiping cloth used for general paper towels or napkins, such as VIVA (product of Scott Corp.), ZEE (product of Crown Zellerbach), etc., are preferable. The thickness of the substrate normally ranges from about 0.5 to about 5.0 mm, preferably from 0.8 to 4.0 mm. The weight of the substrate per 1 $m^2$ ranges from about 20 to about 100 g, preferably from 30 to 80 g.

Examples of the oxidizable metal powder supported by the substrate include iron powder and aluminum powder. Normally, iron powder, such as reduced iron powder, sprayed iron powder, or electrolytic iron powder, is used. The particle size of the oxidizable metal powder normally averages not more than 60 mesh, and the metal powder preferably contains not less than 50% of particles whose sizes are not greater than 100 mesh.

According to the present invention, the substrate supporting the oxidizable metal powder is impregnated with an inorganic electrolyte solution containing activated carbon suspended therein.

The inorganic electrolyte is normally a compound such as a sulfate, a carbonate, a chloride or a hydroxide of an alkali metal, an alkali earth metal or a heavy metal. Among these, a chloride, such as NaCl, KCl, $CaCl_2$, $MgCl_2$, $FeCl_2$ or $FeCl_3$, is preferable.

The activated carbon is used as a reaction assistant and a water-retaining agent, and it may be, for instance, coconut shell carbon, wood meal carbon, bituminous coal, peat or lignite.

If desired, in addition to the activated carbon, zeolite, diatomaceous earth, perlite, vermiculite or a water-absorbing resin may be mixed as a water-retaining agent.

BRIEF DESCRIPTION OF THE DRAWINGS

FIG. 1 is a sectional view of a sheet-shaped heat-generating body;

FIG. 2 is a view schematically showing a sheet-shaped structure of the heat-generating body;

FIGS. 3a to 3d are views showing various forms in which the sheet-shaped heating-generating body may be used;

FIGS. 4 and 5 are graphs showing heat generation curves;

FIG. 6 is a graph showing changes in the temperature of a subject of heating; and FIG. 7 is a graph showing changes in the temperature of a subject of heating according to Example 3.

DETAILED DESCRIPTION OF THE PREFERRED EMBODIMENT

First, a method of manufacturing a sheet-shaped heat-generating body according to the present invention will be described.

A sheet-shaped substrate comprising irregularly arranged fibers and having a multiplicity of gaps among the fibers is prepared. An oxidizable metal powder is uniformly applied on the substrate. Thereafter, the substrate with the metal powder applied thereon is vibrated, thereby causing the metal powder to gradually enter the gaps among the fibers of the substrate, and thus become supported by the substrate. The amount of the metal powder supported normally ranges from about 1 to about 30 g, preferably from 3 to 20 g, per 1 g of the substrate. This amount is adjusted to a prescribed holding amount in accordance with factors such as the amount of the metal powder applied, the vibration strength and the vibration period. The above-described processes whereby the metal powder is dispersed in the gaps and adhered to the fibers enable the metal powder to be supported by the substrate so firmly that the metal powder does not easily separate from the substrate, thereby achieving a sheet-shaped body supporting metal powder, or a sheet-shaped structure, in which the metal powder is integrated with the fibers.

Subsequently, the structure is impregnated with an electrolyte solution containing activated carbon suspended therein, thereby achieving a sheet-shaped heat-generating body. The amount of the electrolyte solution with which the structure is impregnated normally ranges from about 0.2 to about 3.0 g, preferably from 0.5 to 2.0 g, per 1 g of the metal powder in the structure. The ratio by weight between the water, the activated carbon and the electrolyte that are contained in the electrolyte solution is normally 1:0.05 to 0.50:0.01 to 0.20, preferably 1:0.08 to 0.20:0.02 to 0.15.

The impregnation method may be any method so long as the sheet-shaped structure is impregnated with a prescribed amount of an electrolyte solution with activated carbon suspended therein. Examples of impregnation method which may be used include: ① a method of impregnating the sheet-shaped structure with the electrolyte solution by spraying the solution onto the surface of the structure; and ② a method of impregnating the structure with the electrolyte solution by passing the structure through the gap between rollers carrying the activated-carbon-suspended electrolyte solution applied thereon.

When a sheet-shaped heat-generating body according to the present invention has been obtained in this way, the body may be used either in its uncut state or in a state of being cut into a suitable size. Further, the body may be used singly or in a state of being superimposed on another. In order to prevent the heat-generating substance from contaminating the subject which is to be warmed by the heat-generating body, the body is normally used in the state of being covered with air-permeable film or received in a flat-shaped bag.

The material which is used to form the air-permeable cover or bag may be any material so long as the material is capable of supplying air necessary to the heat generation of the heat-generating body inside the cover or bag. Normally used is a non-woven or woven fabric of a natural or synthetic fiber, a paper, a film of varying type of synthetic resin, or a composite sheet of these materials. Specific examples which may be used are: a non-woven or woven fabric of a natural fiber such as cotton, hemp, silk, wool or rayon; and a non-woven or woven fabric of a synthetic fiber such as nylon, polyethylene or polypropylene fiber, polyacrylic fiber, or polyvinyl chloride fiber. Specific examples of synthetic-resin films are: non-air-permeable films of polyethylene, polypropylene, nylon, polyester and polyvinyl chloride which have fine bores formed therein by a needle, laser or electric discharge machining and which are thus rendered air-permeable; and a microporous film intrinsically having numerous micropores preferably having a diameter not more than 20 μm. Among these, the following is preferable: a composite sheet of a non-woven fabric and a synthetic resin film which is rendered air-permeable; a microporous film; a microporous film having part of its micropores coated or heat-sealed to restrict air-permeation through the film; and a combination of a microporous film with either a non-woven fabric or synthetic resin porous film superimposed thereon. As the above-mentioned non-air-permeable film, a composite sheet of one of the above non-air-permeable plastic sheets and non-woven fabric, or an aluminum foil laminated with a plastic film is to be used.

Further, non-adhesive but tackiness agents may be applied to the surface of the non-air-permeable sheet in order that the sheet-shaped heat-generating body can be attached to the user's underwear, if desired.

The heat-generating body in the cover or the bag is further accommodated in and sealed in an outer bag of a non-air-permeable film so as to be stored therein until use.

Next, a sheet-shaped heat-generating body according to the present invention will be specifically described with reference to the drawings.

FIG. 1 illustrates a section of a sheet-shaped heat-generating body, and FIG. 2 schematically illustrates a sheet-shaped structure in which a metal powder is supported by a substrate.

Referring to FIG. 2, a substrate 3 comprising irregularly arranged fibers 1 and having a multiplicity of gaps 2, and a metal powder 4 dispersed in the gaps 2 and supported by the substrate 3 constitute a sheet-shaped structure 5. When an inorganic electrolyte solution containing activated carbon suspended therein is sprayed so as to impregnate the structure 5 with the solution, the metal powder 4, the activated carbon, and the inorganic electrolyte solution are mixed with each other, and are integrated with the substrate 3 to form a sheet-shaped heat-generating body 6. The sheet-shaped heat-generating body 6 is entirely received in a bag 8 having air-permeation holes 7.

The sheet-shaped heat-generating body may be stored as tightly sealed in an outer bag (not shown) made of a non-air-permeable film or the like until the body is used.

Since the sheet-shaped heat-generating body is free from one-sided distribution of the heat-generating substance, and has excellent flexibility, it can be manufactured with various sizes and configurations, which include not only the sizes and the configurations normally adopted for use as portable body warmers but also any other sizes or configurations as desired. Thus, suitable sizes and suitable configurations can be selected in accordance with the intended use.

FIGS. 3a to 3d show examples of various forms in which a sheet-shaped heat-generating body according to the present invention may be used. FIG. 3a illustrates a wrapper form, FIG. 3b illustrates an elongated wrapper form, FIG. 3c illustrates a bag form, and FIG. 3d illustrates a container form.

Since a sheet-shaped heat-generating sheet according to the present invention includes a substrate supporting the heat-generating substance uniformly dispersed therein, the substrate and the heat-generating substance are integrated with each other. Therefore, the heat-generating substance is not displaced or locally distributed. This feature assures that, when the body is worn by the user, the body does not become uncomfortable to wear, and provides uniform heating. Furthermore, the sheet-shaped heat-generating body can be manufactured into a body having a large area. Still further, since the body includes a substrate in which fibers are irregularly arranged with a multiplicity of gaps among the fibers, the body has excellent flexibility, hence, is capable of being formed into any desired configuration according to the intended use, that is, is widely applicable.

EXAMPLES

Example 1

Used as a substrate was a sheet-shaped non-woven fabric (Quinocloth, a product of Honshu Seishi Kabushiki Kaisha) in which pulp fibers were irregularly arranged. The non-woven fabric had: a basis weight of 40 g/m$^2$; a thickness of 1 mm; tensile strengths of 1.6 kg/100 mm (dry) and 0.8 kg/100 mm (wet); elongations of 18% (dry) and 28% (wet); and water retention of 20 times. The substrate was formed into a shape of 20 cm in length and 20 cm in width. 15 g of reduced iron powder containing 60% of particles whose size was not more than 100 mesh was uniformly applied on the surface of the substrate. Then, the substrate with the iron powder thereon was vibrated, thereby obtaining a sheet-shaped structure in which the iron powder was supported by the substrate. Subsequently, 14 g of an aqueous solution of 5 wt % of salt, in which 13 wt % of activated carbon relative to the water was suspended, was sprayed onto the structure, and the resultant structure was pressed by rollers, thereby uniformly impregnating the structure with the solution. A sheet-shaped heat-generating body was obtained in this way. The sheet-shaped heat-generating body was folded into a body having four layers (each having an area of 10×10 cm), and the folded, four-layer body was received in an inner bag comprising a sheet, one face of which was made of a composite sheet of non-woven fabric and microporous film that had a water vapor transmission of 350 g/m$^2$. day, then sealed in a non-air-permeable outer bag to be stored therein.

Next, the sheet-shaped heat-generating body was subjected to tests on heating performance.

The sheet-shaped heat-generating body was taken out from the outer bag, then subjected to a test conducted, in a room at a temperature of 20° C. and a relative humidity of 68%, by the method according to JIS S-4100 As a result, the heat-generation curve shown in FIG. 4 was obtained. The temperature of the subject of heating exceeded 40° C. five minutes after the start of the test, and reached about 60° C. thirty minutes after the start. Heating of the subject to maintain it at temperatures above 40° C. continued about 7 hours.

Example 2

A sheet-shaped structure was obtained by causing 38 g of reduced iron powder to be dispersed in and supported by a substrate by the same method as that used in Example 1, which substrate was made of a sheet-shaped non-woven fabric (Quinocloth) of the same type as that used in Example 1, had dimensions of 27 cm (length)×60 cm (width), and weighed 6.7 g. Subsequently, 27 g of an aqueous solution of 5 wt % of salt, in which 13 wt % of activated carbon relative to the water was suspended, was sprayed onto the structure, and the structure was impregnated with the solution in the same way as that in Example 1, thereby obtaining a sheet-shaped heat-generating body. The sheet-shaped heat-generating body was folded into a body having three layers (each having an area of 27×20 cm), and the folded, three-layer body was received in an inner bag having two surfaces, one being made of aluminum foil, the other being made of a composite sheet of non-woven fabric and microporous film, and having a water vapor transmission of about 475 g/m$^2$. day.

Next, heating performance test was conducted, in a room at a temperature of 20° C. and a relative humidity of 68%, by the method according to JIS S-4100. As a result, the heat-generation curve shown in FIG. 5 was obtained. The temperature of the subject of heating exceeded 40° C. five minutes after the start of the test, and reached about 60° C. 40 minutes after the start. Heating of the subject to maintain it at temperatures above 40° C. continued about 4.5 hours.

Application Example

Sheet-shaped heat-generating bodies, each being the same as that obtained in Example 2, were used to form a warming container of the type shown in FIG. 3d which had a length of 20 cm, a width of 10 cm, and a depth of 5 cm. Subsequently, eight manjus (Japanese food, buns with bean-jam filling), which each had a diameter of 4.5 cm and a height of 4.5 cm, and which were already heated to about 80° C., were received in the container, and the container with the food was entirely covered with a sheet of polyurethane foam which had a thickness of 5 mm. The resultant container was placed in a refrigerator at 0° C. and the temperature of the food was measured with a thermocouple thermometer placed in the center of the food. The result of the measurement is indicated, in FIG. 6, by a temperature curve in a solid line. The food was maintained at temperatures above 50° C. for two hours, and maintained at temperatures above 40° C. for three hours. On the other hand, for the purpose of comparison, another temperature maintaining test was conducted under the same conditions except that the warming container was substituted by a cardboard container normally used to contain food of the type being discussed. The result of this test is indicated, in FIG. 6, by a temperature curve in a broken line. The temperature at the center of the food lowered to 18° C. thirty minutes after the start, and further lowered to 10° C. 1 hour after the start.

Example 3

Used as a substrate was a non-woven fabric (Quinocloth, a product of Honshu Seishi Kabushiki Kaisha) in which pulp fibers were irregularly arranged. The non-woven fabric had: a basis weight of 70 g/m$^2$; a thickness of 1.2 mm; tensile strengths of 3.5 kg/100 mm (dry) and 2.0 kg/100 mm (wet); elongations of 18% (dry) and 27% (wet); and water retention of 20 times. The substrate was formed into a shape of 11.5 cm in length and 17 cm in width. 13 g of reduced iron powder, being the same type as that used in Example 1, was uniformly applied on the surface of the substrate. Then, the substrate with the iron powder thereon was vibrated, thereby obtaining a sheet-shaped structure in which the iron powder was supported by the substrate. Subsequently, 8 g of an aqueous solution of 15 wt % of salt in which 16 wt % of activated carbon relative to the water was suspended was sprayed onto the structure, and the resultant structure was pressed by rollers, thereby uniformly impregnating the structure with the solution. A sheet-shaped heat-generating body was obtained in this way. The sheet-shaped heat-generating body was folded into a body having two layers (each having an area of 8.5×11.5 cm), and the folded, two-layer body was received in an inner bag comprising a sheets one face of which was made of a composite sheet of non-woven fabric and microporous film that had a water vapor transmission of 500 g/m$^2$ . day, the other being made of a composite sheet of non-air-permeable polyethylene and non-woven fabric, then sealed in a non-air-permeable outer bag to be stored therein.

Next, the sheet-shaped heat-generating body was subjected to tests on heating performance as it was in Example 1.

As a result, the heat-generation curve shown in FIG. 7 was obtained. The temperature of the subject of heating exceeded 40° C. ten minutes after the start of the test, and reached about 53° C. thirty minutes after the start. Heating of the subject to maintain it at temperatures above 40° C. continued about 10 hours.

What is claimed is:

1. A sheet-shaped heat generating body comprising:
   a sheet-shaped substrate comprising irregularly arranged fibers produced by a dry method, having a multiplicity of gaps among the fibers, said substrate having a thickness of from 0.5 mm to 5.0 mm, and having a weight of from 20 g/m$^2$ to 100 g/m$^2$;
   an oxidizable metal powder dispersed in and supported by said substrate; and
   an inorganic electrolyte solution containing activated carbon mixed and suspended therein, said substrate supporting said oxidizable metal powder dispersed therein being impregnated with said inorganic electrolyte solution, said heat-generating body being flexible and free from displacement or one-sided distribution of the oxidizable metal powder and inorganic electrolyte solution containing activated carbon.

2. A sheet-shaped heat-generating body according to claim 1, wherein said substrate is made of an organic fiber or an inorganic fiber.

3. A sheet-shaped heat-generating body according to claim 1, wherein said substrate comprises a non-woven fabric.

4. A sheet-shaped heat-generating body according to claim 1, wherein said oxidizable metal powder is an iron powder.

5. A sheet-shaped heat-generating body according to claim 1, wherein said oxidizable metal powder is an aluminum powder.

6. A sheet-shaped heat-generating body according to claim 1, wherein said oxidizable metal powder is contained in an amount of from about 1 to about 30 g per 1 g of said substrate.

7. A sheet-shaped heat-generating body according to claim 1, wherein said inorganic electrolyte is a compound selected from the group consisting of sulfates, carbonates, chlorides and hydroxides of alkali metals, alkali earth metals and heavy metals.

8. A sheet-shaped heat-generating body according to claim 1, wherein said inorganic electrolyte solution with which said substrate is impregnated is contained in an amount of from about 0.2 to about 3.0 g per 1 g of said metal powder.

9. A sheet-shaped heat-generating body according to claim 1, wherein said inorganic electrolyte solution contains water, activated carbon and an electrolyte at a ratio by weight of 1:0.05 to 0.50:0.01 to 0.20.

10. A sheet-shaped heat-generating body according to claim 1, further comprising an air-permeable cover covering said substrate which supports said oxidizable metal powder dispersed therein and which is impregnated with said inorganic electrolyte solution.

11. A sheet-shaped heat-generating body according to claim 10, wherein said air-permeable cover is made of a material selected from the group consisting of a non-woven fabric, a woven fabric, a paper, a non-air-permeable film of a synthetic resin having fine bores formed therein and being rendered air-permeable, and a microporous film intrinsically having numerous micropores.

12. A sheet-shaped heat-generating body according to claim 10, wherein said air-permeable cover is a bag or film having air-permeability on at least one surface thereof.

13. A sheet-shaped heat-generating body according to claim 12, wherein the portion of said air-permeable cover where said cover is air-permeable comprises a composite sheet consisting of a non-woven fabric and an air-permeable synthetic-resin film.

14. A sheet-shaped heat-generating body according to claim 13, wherein said air-permeable synthetic-resin film is a microporous film having a plurality of micropores not greater than about 20 $\mu$m in diameter.

15. A sheet-shaped heat-generating body comprising:
    a sheet-shaped substrate comprising irregularly arranged fibers produced by a dry method, having a multiplicity of gaps among the fibers, said substrate having a thickness of from 0.5 mm to 5.0 mm, and having a weight of from 20 g/m$^2$ to 100 g/m$^2$;
    an oxidizable metal powder dispersed in the gaps and supported by said substrate; and an inorganic electrolyte solution containing activated carbon mixed and suspended therein, said substrate supporting said oxidizable metal powder dispersed therein being impregnated with said inorganic electrolyte solution, said heat-generating body being flexible and free from displacement or one-sided distribution of the oxidizable metal powder and inorganic electrolyte solution containing activated carbon.

* * * * *